(12) United States Patent
Pilletere et al.

(10) Patent No.: US 11,259,841 B2
(45) Date of Patent: Mar. 1, 2022

(54) SEAL ASSEMBLIES FOR SURGICAL ACCESS ASSEMBLIES

(71) Applicant: Covidien LP, Mansfield, MA (US)

(72) Inventors: Roy Pilletere, North Haven, CT (US); Matthew Dinino, Newington, CT (US); Nicolette LaPierre, Windsor Locks, CT (US); Garrett Ebersole, Hamden, CT (US); Jacob Baril, Norwalk, CT (US); George Matta, Plainville, MA (US); Eric Brown, Haddam, CT (US); Kevin Desjardin, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 287 days.

(21) Appl. No.: 16/448,968

(22) Filed: Jun. 21, 2019

(65) Prior Publication Data

US 2020/0397474 A1 Dec. 24, 2020

(51) Int. Cl.
*A61B 17/34* (2006.01)

(52) U.S. Cl.
CPC ...... *A61B 17/3462* (2013.01); *A61B 17/3423* (2013.01); *A61B 17/3498* (2013.01)

(58) Field of Classification Search
CPC ............ A61B 17/3462; A61B 17/3423; A61B 17/3498; A61B 2017/3464
See application file for complete search history.

(56) References Cited

U.S. PATENT DOCUMENTS

| | | |
|---|---|---|
| 3,402,710 A | 9/1968 | Paleschuck |
| 3,495,586 A | 2/1970 | Regenbogen |
| 4,016,884 A | 4/1977 | Kwan-Gett |
| 4,112,932 A | 9/1978 | Chiulli |
| 4,183,357 A | 1/1980 | Bentley et al. |
| 4,356,826 A | 11/1982 | Kubota |
| 4,402,683 A | 9/1983 | Kopman |
| 4,653,476 A | 3/1987 | Bonnet |
| 4,737,148 A | 4/1988 | Blake |
| 4,863,430 A | 9/1989 | Klyce et al. |
| 4,863,438 A | 9/1989 | Gauderer et al. |
| 4,984,564 A | 1/1991 | Yuen |
| 5,002,557 A | 3/1991 | Hasson |

(Continued)

FOREIGN PATENT DOCUMENTS

| | | |
|---|---|---|
| CA | 2702419 A1 | 11/2010 |
| EP | 0226026 A2 | 6/1987 |

(Continued)

OTHER PUBLICATIONS

European Search Report dated Nov. 5, 2020, corresponding to counterpart European Application No. 20180351.7; 7 pages.

*Primary Examiner* — Alexander J Orkin
(74) *Attorney, Agent, or Firm* — Carter, DeLuca & Farrell LLP

(57) ABSTRACT

Access assemblies includes an instrument valve housing and a valve assembly disposed within the cavity of the instrument valve housing. The valve assembly includes a guard assembly, and a seal assembly disposed distal of the guard assembly. In embodiments, the seal assembly includes a plurality of seal segments in an overlapping configuration. Each seal segment of the plurality of seal segments includes a seal portion having a smooth surface and a ribbed surface. The ribbed surfaces include a plurality of ribs extending in a radial direction.

18 Claims, 9 Drawing Sheets

(56) References Cited

U.S. PATENT DOCUMENTS

| | | |
|---|---|---|
| 5,073,169 A | 12/1991 | Raiken |
| 5,082,005 A | 1/1992 | Kaldany |
| 5,122,122 A | 6/1992 | Allgood |
| 5,159,921 A | 11/1992 | Hoover |
| 5,176,697 A | 1/1993 | Hasson et al. |
| 5,183,471 A | 2/1993 | Wilk |
| 5,192,301 A | 3/1993 | Kamiya et al. |
| 5,209,737 A * | 5/1993 | Ritchart ............ A61B 17/3462 604/167.03 |
| 5,209,741 A | 5/1993 | Spaeth |
| 5,209,754 A | 5/1993 | Ahluwalia |
| 5,217,466 A | 6/1993 | Hasson |
| 5,242,409 A | 9/1993 | Buelna |
| 5,242,415 A | 9/1993 | Kantrowitz et al. |
| 5,257,973 A | 11/1993 | Villasuso |
| 5,257,975 A | 11/1993 | Foshee |
| 5,269,772 A | 12/1993 | Wilk |
| 5,290,249 A | 3/1994 | Foster et al. |
| 5,312,391 A | 5/1994 | Wilk |
| 5,312,417 A | 5/1994 | Wilk |
| 5,314,417 A | 5/1994 | Stephens et al. |
| 5,318,516 A | 6/1994 | Cosmescu |
| 5,330,486 A | 7/1994 | Wilk |
| 5,334,143 A | 8/1994 | Carroll |
| 5,336,169 A | 8/1994 | Divilio et al. |
| 5,336,203 A | 8/1994 | Goldhardt et al. |
| 5,337,937 A | 8/1994 | Remiszewski et al. |
| 5,342,315 A | 8/1994 | Rowe et al. |
| 5,345,927 A | 9/1994 | Bonutti |
| 5,360,417 A | 11/1994 | Gravener et al. |
| 5,366,478 A | 11/1994 | Brinkerhoff et al. |
| 5,375,588 A | 12/1994 | Yoon |
| 5,378,588 A | 1/1995 | Tsuchiya |
| 5,391,156 A | 2/1995 | Hildwein et al. |
| 5,394,863 A | 3/1995 | Sanford et al. |
| 5,395,367 A | 3/1995 | Wilk |
| 5,411,483 A * | 5/1995 | Loomas ............ A61B 17/3462 604/167.06 |
| 5,437,683 A | 8/1995 | Neumann et al. |
| 5,445,615 A | 8/1995 | Yoon |
| 5,451,222 A | 9/1995 | De Maagd et al. |
| 5,460,170 A | 10/1995 | Hammerslag |
| 5,464,409 A | 11/1995 | Mohajer |
| 5,480,410 A | 1/1996 | Cuschieri et al. |
| 5,490,843 A | 2/1996 | Hildwein et al. |
| 5,507,758 A | 4/1996 | Thomason et al. |
| 5,511,564 A | 4/1996 | Wilk |
| 5,514,133 A | 5/1996 | Golub et al. |
| 5,514,153 A | 5/1996 | Bonutti |
| 5,520,698 A | 5/1996 | Koh |
| 5,522,791 A | 6/1996 | Leyva |
| 5,524,644 A | 6/1996 | Crook |
| 5,540,648 A | 7/1996 | Yoon |
| 5,545,150 A | 8/1996 | Danks et al. |
| 5,545,179 A | 8/1996 | Williamson, IV |
| 5,556,385 A | 9/1996 | Andersen |
| 5,569,159 A | 10/1996 | Anderson et al. |
| 5,577,993 A | 11/1996 | Zhu et al. |
| 5,601,581 A | 2/1997 | Fogarty et al. |
| 5,624,399 A | 4/1997 | Ackerman |
| 5,634,911 A | 6/1997 | Hermann et al. |
| 5,634,937 A | 6/1997 | Mollenauer et al. |
| 5,643,285 A | 7/1997 | Rowden et al. |
| 5,649,550 A | 7/1997 | Crook |
| 5,651,771 A | 7/1997 | Tangherlini et al. |
| 5,653,705 A | 8/1997 | de la Torre et al. |
| 5,656,013 A | 8/1997 | Yoon |
| 5,672,168 A | 9/1997 | de la Torre et al. |
| 5,683,378 A | 11/1997 | Christy |
| 5,685,857 A | 11/1997 | Negus et al. |
| 5,697,946 A | 12/1997 | Hopper et al. |
| 5,709,675 A | 1/1998 | Williams |
| 5,713,858 A | 2/1998 | Heruth et al. |
| 5,713,869 A | 2/1998 | Morejon |
| 5,722,962 A | 3/1998 | Garcia |
| 5,728,103 A | 3/1998 | Picha et al. |
| 5,730,748 A | 3/1998 | Fogarty et al. |
| 5,735,791 A | 4/1998 | Alexander, Jr. et al. |
| 5,741,298 A | 4/1998 | MacLeod |
| 5,752,970 A | 5/1998 | Yoon |
| 5,782,817 A | 7/1998 | Franzel et al. |
| 5,795,290 A | 8/1998 | Bridges |
| 5,803,921 A | 9/1998 | Bonadio |
| 5,810,712 A | 9/1998 | Dunn |
| 5,813,409 A | 9/1998 | Leahy et al. |
| 5,830,191 A | 11/1998 | Hildwein et al. |
| 5,836,871 A | 11/1998 | Wallace et al. |
| 5,836,913 A | 11/1998 | Orth et al. |
| 5,840,077 A | 11/1998 | Rowden et al. |
| 5,842,971 A | 12/1998 | Yoon |
| 5,848,992 A | 12/1998 | Hart et al. |
| 5,853,417 A | 12/1998 | Fogarty et al. |
| 5,857,461 A | 1/1999 | Levitsky et al. |
| 5,865,817 A | 2/1999 | Moenning et al. |
| 5,871,474 A | 2/1999 | Hermann et al. |
| 5,876,413 A | 3/1999 | Fogarty et al. |
| 5,894,843 A | 4/1999 | Benetti et al. |
| 5,895,377 A | 4/1999 | Smith et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,914,415 A | 6/1999 | Tago |
| 5,916,198 A | 6/1999 | Dillow |
| 5,941,898 A | 8/1999 | Moenning et al. |
| 5,951,588 A | 9/1999 | Moenning |
| 5,957,913 A | 9/1999 | de la Torre et al. |
| 5,964,781 A | 10/1999 | Mollenauer et al. |
| 5,976,174 A | 11/1999 | Ruiz |
| 5,997,515 A | 12/1999 | de la Torre et al. |
| 6,017,355 A | 1/2000 | Hessel et al. |
| 6,018,094 A | 1/2000 | Fox |
| 6,024,736 A | 2/2000 | de la Torre et al. |
| 6,030,402 A | 2/2000 | Thompson et al. |
| 6,033,426 A | 3/2000 | Kaji |
| 6,033,428 A | 3/2000 | Sardella |
| 6,042,573 A | 3/2000 | Lucey |
| 6,048,309 A | 4/2000 | Flom et al. |
| 6,059,816 A | 5/2000 | Moenning |
| 6,068,639 A | 5/2000 | Fogarty et al. |
| 6,077,288 A | 6/2000 | Shimomura et al. |
| 6,086,603 A | 7/2000 | Termin et al. |
| 6,099,506 A | 8/2000 | Macoviak et al. |
| 6,110,154 A | 8/2000 | Shimomura et al. |
| 6,142,936 A | 11/2000 | Beane et al. |
| 6,156,006 A | 12/2000 | Brosens et al. |
| 6,162,196 A | 12/2000 | Hart et al. |
| 6,171,282 B1 | 1/2001 | Ragsdale |
| 6,197,002 B1 | 3/2001 | Peterson |
| 6,217,555 B1 | 4/2001 | Hart et al. |
| 6,228,063 B1 | 5/2001 | Aboul-Hosn |
| 6,234,958 B1 | 5/2001 | Snoke et al. |
| 6,238,373 B1 | 5/2001 | de la Torre et al. |
| 6,241,768 B1 | 6/2001 | Agarwal et al. |
| 6,251,119 B1 | 6/2001 | Addis |
| 6,254,534 B1 | 7/2001 | Butler et al. |
| 6,264,604 B1 | 7/2001 | Kieturakis et al. |
| 6,276,661 B1 | 8/2001 | Laird |
| 6,293,952 B1 | 9/2001 | Brosens et al. |
| 6,315,770 B1 | 11/2001 | de la Torre et al. |
| 6,319,246 B1 | 11/2001 | de la Torre et al. |
| 6,328,720 B1 | 12/2001 | McNally et al. |
| 6,329,637 B1 | 12/2001 | Hembree et al. |
| 6,371,968 B1 | 4/2002 | Kogasaka et al. |
| 6,382,211 B1 | 5/2002 | Crook |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |

(56) References Cited

U.S. PATENT DOCUMENTS

| | | |
|---|---|---|
| 6,485,410 B1 | 11/2002 | Loy |
| 6,488,620 B1 | 12/2002 | Segermark et al. |
| 6,488,692 B1 | 12/2002 | Spence et al. |
| 6,524,283 B1 | 2/2003 | Hopper et al. |
| 6,527,787 B1 | 3/2003 | Fogarty et al. |
| 6,544,210 B1 | 4/2003 | Trudel et al. |
| 6,551,270 B1 | 4/2003 | Bimbo et al. |
| 6,558,371 B2 | 5/2003 | Dorn |
| 6,562,022 B2 | 5/2003 | Hoste et al. |
| 6,569,120 B1 | 5/2003 | Green et al. |
| 6,572,631 B1 | 6/2003 | McCartney |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,589,316 B1 | 7/2003 | Schultz et al. |
| 6,592,543 B1 | 7/2003 | Wortrich et al. |
| 6,613,952 B2 | 9/2003 | Rambo |
| 6,623,426 B2 | 9/2003 | Bonadio et al. |
| 6,669,674 B1 | 12/2003 | Macoviak et al. |
| 6,676,639 B1 | 1/2004 | Ternstrom |
| 6,684,405 B2 | 2/2004 | Lezdey |
| 6,702,787 B2 | 3/2004 | Racenet et al. |
| 6,706,050 B1 | 3/2004 | Giannadakis |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,800,084 B2 | 10/2004 | Davison et al. |
| 6,811,546 B1 | 11/2004 | Callas et al. |
| 6,814,078 B2 | 11/2004 | Crook |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,863,674 B2 | 3/2005 | Kasahara et al. |
| 6,878,110 B2 | 4/2005 | Yang et al. |
| 6,884,253 B1 | 4/2005 | McFarlane |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,942,633 B2 | 9/2005 | Odland |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,986,752 B2 | 1/2006 | McGuckin, Jr. et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,011,645 B2 | 3/2006 | McGuckin, Jr. et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,100,614 B2 | 9/2006 | Stevens et al. |
| 7,101,353 B2 | 9/2006 | Lui et al. |
| 7,104,981 B2 | 9/2006 | Elkins et al. |
| 7,153,261 B2 | 12/2006 | Wenchell |
| 7,160,309 B2 | 1/2007 | Voss |
| 7,163,510 B2 | 1/2007 | Kahle et al. |
| 7,192,436 B2 | 3/2007 | Sing et al. |
| 7,195,590 B2 | 3/2007 | Butler et al. |
| 7,201,725 B1 | 4/2007 | Cragg et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,064 B2 | 6/2007 | Hopper et al. |
| 7,235,084 B2 | 6/2007 | Skakoon et al. |
| 7,238,154 B2 | 7/2007 | Ewers et al. |
| 7,258,712 B2 | 8/2007 | Schultz et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,300,448 B2 | 11/2007 | Criscuolo et al. |
| 7,316,699 B2 | 1/2008 | McFarlane |
| 7,331,940 B2 | 2/2008 | Sommerich |
| 7,344,547 B2 | 3/2008 | Piskun |
| 7,377,898 B2 | 5/2008 | Ewers et al. |
| 7,390,322 B2 | 6/2008 | McGuckin, Jr. et al. |
| 7,393,322 B2 | 7/2008 | Wenchell |
| 7,412,977 B2 | 8/2008 | Fields et al. |
| 7,440,661 B2 | 10/2008 | Kobayashi |
| 7,445,597 B2 | 11/2008 | Butler et al. |
| 7,452,363 B2 | 11/2008 | Ortiz |
| 7,473,221 B2 | 1/2009 | Ewers et al. |
| 7,481,765 B2 | 1/2009 | Ewers et al. |
| 7,493,703 B2 | 2/2009 | Kim et al. |
| 7,513,361 B1 | 4/2009 | Mills, Jr. |
| 7,513,461 B2 | 4/2009 | Reutenauer et al. |
| 7,520,876 B2 | 4/2009 | Ressemann et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,608,082 B2 | 10/2009 | Cuevas et al. |
| 7,625,361 B2 | 12/2009 | Suzuki et al. |
| 7,645,232 B2 | 1/2010 | Shluzas |
| 7,650,887 B2 | 1/2010 | Nguyen et al. |
| 7,704,207 B2 | 4/2010 | Albrecht et al. |
| 7,717,846 B2 | 5/2010 | Zirps et al. |
| 7,717,847 B2 | 5/2010 | Smith |
| 7,721,742 B2 | 5/2010 | Kalloo et al. |
| 7,727,146 B2 | 6/2010 | Albrecht et al. |
| 7,730,629 B2 | 6/2010 | Kim |
| 7,736,306 B2 | 6/2010 | Brustad et al. |
| 7,753,901 B2 | 7/2010 | Piskun et al. |
| 7,758,500 B2 | 7/2010 | Boyd et al. |
| 7,762,995 B2 | 7/2010 | Eversull et al. |
| 7,766,824 B2 | 8/2010 | Jensen et al. |
| 7,787,963 B2 | 8/2010 | Geistert et al. |
| 7,798,998 B2 | 9/2010 | Thompson et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,846,123 B2 | 12/2010 | Vassiliades et al. |
| 7,850,600 B1 | 12/2010 | Piskun |
| 7,850,667 B2 | 12/2010 | Gresham |
| 7,867,164 B2 | 1/2011 | Butler et al. |
| 7,896,889 B2 | 3/2011 | Mazzocchi et al. |
| 7,905,829 B2 | 3/2011 | Nishimura et al. |
| 7,909,760 B2 | 3/2011 | Albrecht et al. |
| 7,913,697 B2 | 3/2011 | Nguyen et al. |
| 7,951,076 B2 | 5/2011 | Hart et al. |
| 7,955,257 B2 | 6/2011 | Frasier et al. |
| 7,955,313 B2 | 6/2011 | Boismier |
| 7,998,068 B2 | 8/2011 | Bonadio et al. |
| 8,021,296 B2 | 9/2011 | Bonadio et al. |
| 8,025,670 B2 | 9/2011 | Sharp et al. |
| 8,038,652 B2 | 10/2011 | Morrison et al. |
| 8,066,673 B2 | 11/2011 | Hart et al. |
| 8,079,986 B2 | 12/2011 | Taylor et al. |
| 8,092,430 B2 | 1/2012 | Richard et al. |
| 8,105,234 B2 | 1/2012 | Ewers et al. |
| 8,109,873 B2 | 2/2012 | Albrecht et al. |
| 8,157,786 B2 | 4/2012 | Miller et al. |
| 8,157,817 B2 | 4/2012 | Bonadio et al. |
| 8,187,177 B2 | 5/2012 | Kahle et al. |
| 8,187,178 B2 | 5/2012 | Bonadio et al. |
| 8,241,209 B2 | 8/2012 | Shelton, IV et al. |
| 8,262,568 B2 | 9/2012 | Albrecht et al. |
| 8,323,184 B2 | 12/2012 | Spiegal et al. |
| 8,335,783 B2 | 12/2012 | Milby |
| 8,343,047 B2 | 1/2013 | Albrecht et al. |
| 8,353,824 B2 | 1/2013 | Shelton, IV et al. |
| 8,403,889 B2 | 3/2013 | Richard |
| 8,480,683 B2 | 7/2013 | Fowler et al. |
| 8,574,153 B2 | 11/2013 | Richard |

(56) References Cited

U.S. PATENT DOCUMENTS

| | | |
|---|---|---|
| 8,579,807 B2 | 11/2013 | Moreno, Jr. et al. |
| 8,585,632 B2 | 11/2013 | Okoniewski |
| 2001/0037053 A1 | 11/2001 | Bonadio et al. |
| 2002/0055714 A1 | 5/2002 | Rothschild |
| 2003/0014076 A1 | 1/2003 | Mollenauer et al. |
| 2003/0093104 A1 | 5/2003 | Bonner et al. |
| 2003/0187376 A1 | 10/2003 | Rambo |
| 2003/0187397 A1* | 10/2003 | Vitali ............... A61B 17/3462 604/167.02 |
| 2003/0233115 A1 | 12/2003 | Eversull et al. |
| 2003/0236549 A1 | 12/2003 | Bonadio et al. |
| 2004/0059297 A1 | 3/2004 | Racenet et al. |
| 2004/0092795 A1 | 5/2004 | Bonadio et al. |
| 2004/0102804 A1 | 5/2004 | Chin |
| 2004/0111061 A1 | 6/2004 | Curran |
| 2004/0138529 A1 | 7/2004 | Wiltshire et al. |
| 2004/0204734 A1 | 10/2004 | Wagner et al. |
| 2004/0267096 A1 | 12/2004 | Caldwell et al. |
| 2005/0020884 A1 | 1/2005 | Hart et al. |
| 2005/0070935 A1 | 3/2005 | Ortiz |
| 2005/0096695 A1 | 5/2005 | Olich |
| 2005/0119525 A1 | 6/2005 | Takemoto |
| 2005/0137459 A1 | 6/2005 | Chin et al. |
| 2005/0148823 A1 | 7/2005 | Vaugh et al. |
| 2005/0192483 A1 | 9/2005 | Bonadio et al. |
| 2005/0203346 A1 | 9/2005 | Bonadio et al. |
| 2005/0209608 A1 | 9/2005 | O'Heeron |
| 2005/0245876 A1 | 11/2005 | Khosravi et al. |
| 2005/0251092 A1 | 11/2005 | Howell et al. |
| 2005/0277946 A1 | 12/2005 | Greenhalgh |
| 2006/0071432 A1 | 4/2006 | Staudner |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0212063 A1 | 9/2006 | Wilk |
| 2006/0224161 A1 | 10/2006 | Bhattacharyya |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0270911 A1 | 11/2006 | Voegele et al. |
| 2007/0093695 A1 | 4/2007 | Bonadio et al. |
| 2007/0118175 A1 | 5/2007 | Butler et al. |
| 2007/0151566 A1 | 7/2007 | Kahle et al. |
| 2007/0203398 A1 | 8/2007 | Bonadio et al. |
| 2007/0208312 A1 | 9/2007 | Norton et al. |
| 2007/0225650 A1 | 9/2007 | Hart et al. |
| 2007/0270654 A1 | 11/2007 | Pignato et al. |
| 2007/0270882 A1 | 11/2007 | Hjelle et al. |
| 2008/0009826 A1 | 1/2008 | Miller et al. |
| 2008/0021360 A1 | 1/2008 | Fihe et al. |
| 2008/0027476 A1 | 1/2008 | Piskun |
| 2008/0048011 A1 | 2/2008 | Weller |
| 2008/0091143 A1 | 4/2008 | Taylor et al. |
| 2008/0097162 A1 | 4/2008 | Bonadio et al. |
| 2008/0097332 A1 | 4/2008 | Greenhalgh et al. |
| 2008/0119868 A1 | 5/2008 | Sharp et al. |
| 2008/0161826 A1 | 7/2008 | Guiraudon |
| 2008/0188868 A1 | 8/2008 | Weitzner et al. |
| 2008/0194973 A1 | 8/2008 | Imam |
| 2008/0200767 A1 | 8/2008 | Ewers et al. |
| 2008/0255519 A1 | 10/2008 | Piskun et al. |
| 2008/0294113 A1* | 11/2008 | Brockmeier ....... A61B 17/3498 604/167.06 |
| 2008/0319261 A1 | 12/2008 | Lucini et al. |
| 2009/0005799 A1* | 1/2009 | Franer ............... A61B 17/3462 606/185 |
| 2009/0012477 A1 | 1/2009 | Norton et al. |
| 2009/0036738 A1 | 2/2009 | Cuschieri et al. |
| 2009/0036745 A1 | 2/2009 | Bonadio et al. |
| 2009/0093752 A1 | 4/2009 | Richard et al. |
| 2009/0093850 A1 | 4/2009 | Richard |
| 2009/0105635 A1 | 4/2009 | Bettuchi et al. |
| 2009/0131751 A1 | 5/2009 | Spivey et al. |
| 2009/0137879 A1 | 5/2009 | Ewers et al. |
| 2009/0182279 A1 | 7/2009 | Wenchell et al. |
| 2009/0182288 A1 | 7/2009 | Spenciner |
| 2009/0187079 A1 | 7/2009 | Albrecht et al. |
| 2009/0204067 A1 | 8/2009 | Abu-Halawa |
| 2009/0221968 A1 | 9/2009 | Morrison et al. |
| 2009/0227843 A1 | 9/2009 | Smith et al. |
| 2009/0270813 A1* | 10/2009 | Moreno, Jr ........ A61B 17/3462 604/167.01 |
| 2009/0326330 A1 | 12/2009 | Bonadio et al. |
| 2009/0326332 A1 | 12/2009 | Carter |
| 2010/0004599 A1* | 1/2010 | Zhou ................. A61B 17/3421 604/167.04 |
| 2010/0063452 A1 | 3/2010 | Edelman et al. |
| 2010/0100043 A1 | 4/2010 | Racenet |
| 2010/0113886 A1 | 5/2010 | Piskun et al. |
| 2010/0185153 A1 | 7/2010 | Sugiki et al. |
| 2010/0228094 A1 | 9/2010 | Ortiz et al. |
| 2010/0240960 A1 | 9/2010 | Richard |
| 2010/0249515 A1* | 9/2010 | Hudon ............... A61B 17/3498 600/201 |
| 2010/0249516 A1 | 9/2010 | Shelton, IV et al. |
| 2010/0249523 A1 | 9/2010 | Spiegal et al. |
| 2010/0249524 A1 | 9/2010 | Ransden et al. |
| 2010/0262080 A1 | 10/2010 | Shelton, IV et al. |
| 2010/0280326 A1 | 11/2010 | Hess et al. |
| 2010/0286484 A1 | 11/2010 | Stellon et al. |
| 2010/0286506 A1 | 11/2010 | Ransden et al. |
| 2010/0298646 A1 | 11/2010 | Stellon et al. |
| 2010/0312063 A1 | 12/2010 | Hess et al. |
| 2011/0009704 A1 | 1/2011 | Marczyk et al. |
| 2011/0021877 A1 | 1/2011 | Fortier et al. |
| 2011/0028891 A1 | 2/2011 | Okoniewski |
| 2011/0034778 A1 | 2/2011 | Kleyman |
| 2011/0054257 A1 | 3/2011 | Stopek |
| 2011/0054258 A1 | 3/2011 | O'Keefe et al. |
| 2011/0054260 A1 | 3/2011 | Albrecht et al. |
| 2011/0082341 A1 | 4/2011 | Kleyman et al. |
| 2011/0082343 A1 | 4/2011 | Okoniewski |
| 2011/0082346 A1 | 4/2011 | Stopek |
| 2011/0118553 A1 | 5/2011 | Stopek |
| 2011/0124968 A1 | 5/2011 | Kleyman |
| 2011/0124969 A1 | 5/2011 | Stopek |
| 2011/0124970 A1 | 5/2011 | Kleyman |
| 2011/0125186 A1 | 5/2011 | Fowler et al. |
| 2011/0166423 A1 | 7/2011 | Farascioni et al. |
| 2011/0237899 A1* | 9/2011 | Battles .............. A61B 17/3462 600/208 |
| 2011/0251463 A1 | 10/2011 | Kleyman |
| 2011/0251464 A1 | 10/2011 | Kleyman |
| 2011/0251465 A1 | 10/2011 | Kleyman |
| 2011/0251466 A1 | 10/2011 | Kleyman et al. |
| 2011/0251560 A1 | 10/2011 | Albrecht et al. |
| 2011/0313250 A1 | 12/2011 | Kleyman |
| 2012/0059640 A1 | 3/2012 | Roy et al. |
| 2012/0083661 A1 | 4/2012 | Rockrohr |
| 2012/0130177 A1 | 5/2012 | Davis |
| 2012/0130181 A1 | 5/2012 | Davis |
| 2012/0130182 A1 | 5/2012 | Rodrigues, Jr. et al. |
| 2012/0130183 A1 | 5/2012 | Barnes |
| 2012/0130184 A1 | 5/2012 | Richard |
| 2012/0130185 A1 | 5/2012 | Pribanic |
| 2012/0130186 A1 | 5/2012 | Stopek et al. |
| 2012/0130187 A1 | 5/2012 | Okoniewski |
| 2012/0130188 A1 | 5/2012 | Okoniewski |
| 2012/0130190 A1 | 5/2012 | Kasvikis |
| 2012/0130191 A1 | 5/2012 | Pribanic |
| 2012/0149987 A1 | 6/2012 | Richard et al. |
| 2012/0157777 A1 | 6/2012 | Okoniewski |
| 2012/0157779 A1 | 6/2012 | Fischvogt |
| 2012/0157780 A1 | 6/2012 | Okoniewski et al. |
| 2012/0157781 A1 | 6/2012 | Kleyman |
| 2012/0157782 A1 | 6/2012 | Alfieri |
| 2012/0157783 A1 | 6/2012 | Okoniewski et al. |

(56) References Cited

U.S. PATENT DOCUMENTS

| | | |
|---|---|---|
| 2012/0157784 A1 | 6/2012 | Kleyman et al. |
| 2012/0157785 A1 | 6/2012 | Kleyman |
| 2012/0157786 A1 | 6/2012 | Pribanic |
| 2012/0190931 A1 | 7/2012 | Stopek |
| 2012/0190932 A1 | 7/2012 | Okoniewski |
| 2012/0190933 A1 | 7/2012 | Kleyman |
| 2012/0209077 A1 | 8/2012 | Racenet |
| 2012/0209078 A1 | 8/2012 | Pribanic et al. |
| 2012/0245427 A1 | 9/2012 | Kleyman |
| 2012/0245429 A1 | 9/2012 | Smith |
| 2012/0245430 A1 | 9/2012 | Kleyman et al. |
| 2012/0283520 A1 | 11/2012 | Kleyman |
| 2013/0225930 A1 | 8/2013 | Smith |
| 2013/0225931 A1 | 8/2013 | Cruz et al. |
| 2013/0245373 A1 | 9/2013 | Okoniewski |
| 2013/0274559 A1 | 10/2013 | Fowler et al. |
| 2013/0310651 A1 | 11/2013 | Alfieri |
| 2014/0018632 A1 | 1/2014 | Kleyman |
| 2015/0025477 A1 | 1/2015 | Evans |
| 2015/0223833 A1 | 8/2015 | Coffeen et al. |
| 2019/0059938 A1 | 2/2019 | Holsten |
| 2019/0059944 A1 | 2/2019 | Holsten |
| 2020/0253634 A1* | 8/2020 | Pilletere ............. A61B 17/3462 |
| 2020/0337723 A1* | 10/2020 | Vaccarella ......... A61B 17/3423 |

FOREIGN PATENT DOCUMENTS

| | | |
|---|---|---|
| EP | 0538060 A1 | 4/1993 |
| EP | 0577400 A1 | 1/1994 |
| EP | 0630660 A1 | 12/1994 |
| EP | 0807416 A2 | 11/1997 |
| EP | 0950376 A1 | 10/1999 |
| EP | 1188415 A2 | 3/2002 |
| EP | 1312318 A1 | 5/2003 |
| EP | 1774918 A1 | 4/2007 |
| EP | 1932485 A1 | 6/2008 |
| EP | 2044889 A1 | 4/2009 |
| EP | 2044897 A1 | 4/2009 |
| EP | 2080494 A1 | 7/2009 |
| EP | 2095781 A2 | 9/2009 |
| EP | 2098182 A2 | 9/2009 |
| EP | 2138117 A1 | 12/2009 |
| EP | 2138118 A2 | 12/2009 |
| EP | 2181657 A2 | 5/2010 |
| EP | 2226025 A1 | 9/2010 |
| EP | 2229900 A1 | 9/2010 |
| EP | 2238924 A1 | 10/2010 |
| EP | 2238925 A1 | 10/2010 |
| EP | 2238926 A2 | 10/2010 |
| EP | 2238933 A1 | 10/2010 |
| EP | 2248478 A1 | 11/2010 |
| EP | 2248482 A1 | 11/2010 |
| EP | 2253283 A1 | 11/2010 |
| EP | 2272450 A2 | 1/2011 |
| EP | 2277464 A1 | 1/2011 |
| EP | 2289438 A1 | 3/2011 |
| EP | 2292165 | 3/2011 |
| EP | 2343019 | 7/2011 |
| EP | 3242615 A1 | 11/2017 |
| GB | 2469083 | 4/2009 |
| WO | 8401512 | 4/1984 |
| WO | 9314801 | 8/1993 |
| WO | 9404067 | 3/1994 |
| WO | 9610963 | 4/1996 |
| WO | 9636283 | 11/1996 |
| WO | 9733520 | 9/1997 |
| WO | 9742889 | 11/1997 |
| WO | 9916368 | 4/1999 |
| WO | 9922804 | 5/1999 |
| WO | 9929250 | 6/1999 |
| WO | 0032116 | 6/2000 |
| WO | 0032120 | 6/2000 |
| WO | 0054675 | 9/2000 |
| WO | 0108581 | 2/2001 |
| WO | 0149363 | 7/2001 |
| WO | 0207611 | 1/2002 |
| WO | 03034908 A2 | 5/2003 |
| WO | 03071926 | 9/2003 |
| WO | 03077726 | 9/2003 |
| WO | 2004043275 | 5/2004 |
| WO | 2004054456 | 7/2004 |
| WO | 2004075741 | 9/2004 |
| WO | 2004075930 | 9/2004 |
| WO | 2005058409 | 6/2005 |
| WO | 2006019723 | 2/2006 |
| WO | 2006100658 A2 | 9/2006 |
| WO | 2006110733 | 10/2006 |
| WO | 2007018458 | 2/2007 |
| WO | 2007095703 | 8/2007 |
| WO | 2007143200 | 12/2007 |
| WO | 2008015566 A2 | 2/2008 |
| WO | 2008042005 | 4/2008 |
| WO | 2008077080 | 6/2008 |
| WO | 2008093313 | 8/2008 |
| WO | 2008103151 | 8/2008 |
| WO | 2008121294 A1 | 10/2008 |
| WO | 2008147644 | 12/2008 |
| WO | 2009036343 | 3/2009 |
| WO | 2009052744 A1 | 4/2009 |
| WO | 2010000047 | 1/2010 |
| WO | 2010141409 | 12/2010 |
| WO | 2010141673 | 12/2010 |
| WO | 2012131746 A1 | 10/2012 |
| WO | 2014052532 A1 | 4/2014 |
| WO | 2014116889 A1 | 7/2014 |
| WO | 2016110720 A1 | 7/2016 |
| WO | 2016186905 A1 | 11/2016 |

* cited by examiner

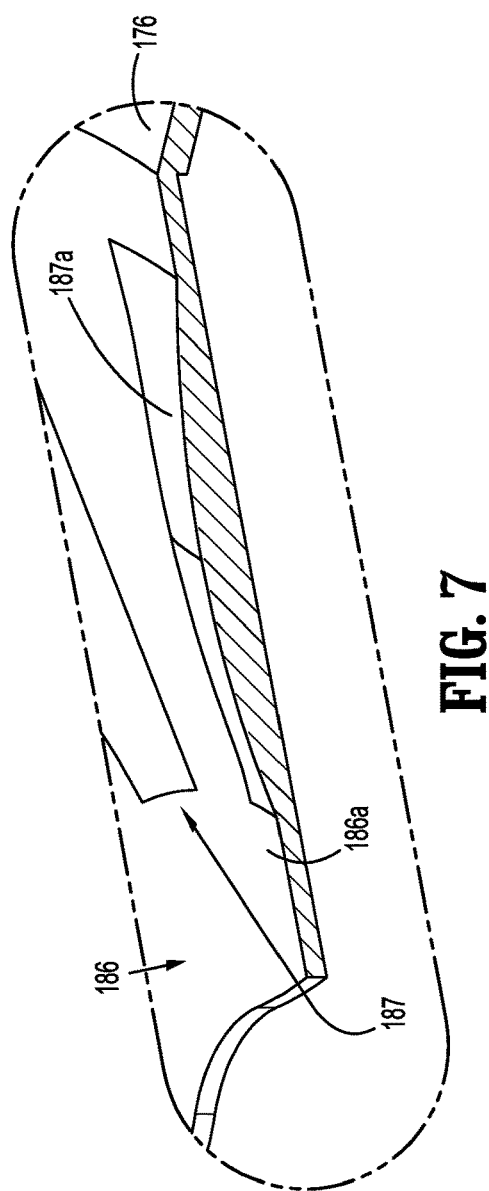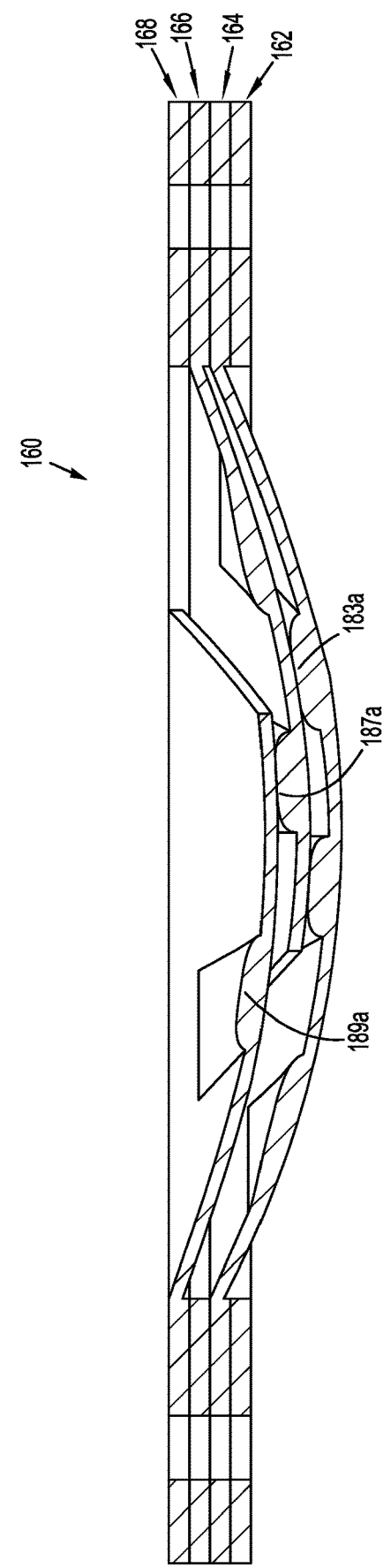

SEAL ASSEMBLIES FOR SURGICAL ACCESS ASSEMBLIES

FIELD

The present disclosure relates to surgical access assemblies for minimally invasive surgery. More particularly, the present disclosure relates to valve assemblies for surgical access assemblies.

BACKGROUND

In order to facilitate minimally invasive surgery, a working space must be created in a desired surgical site. An insufflation fluid, typically $CO_2$, is introduced into the abdomen of the patient to create an inflated state called a pneumoperitoneum. Surgical access assemblies are utilized to allow the introduction of surgical instrumentation and endoscopes (or other visualization tools). These surgical access assemblies maintain the pressure for the pneumoperitoneum, as they have one or more seals that adapt to the surgical instrumentation. Typically, a "zero-seal" in the surgical access assembly seals the surgical access assembly in the absence of a surgical instrument in the surgical access assembly, and an instrument seal seals around a surgical instrument that has been inserted through the surgical access assembly.

The breadth of surgical instrumentation on the market today requires a robust instrument seal capable adjusting to multiple sizes and withstanding multiple insertions and removals of surgical instrumentation. Some of the instrumentation can include sharp edges that can tear or otherwise damage instrument seals. Therefore, it would be beneficial to have a surgical access assembly with improved instrument seal durability.

SUMMARY

An access assembly includes an instrument valve housing, and a valve assembly disposed within the cavity of the instrument valve housing. The instrument valve housing including upper, lower, and inner housing sections and defining a cavity. The valve assembly includes a guard assembly, and a seal assembly disposed distal of the guard assembly. The seal assembly includes a plurality of seal segments in an overlapping configuration. Each seal segment of the plurality of seal segments includes a seal portion having a smooth surface and a ribbed surface. The ribbed surfaces include a plurality of ribs extending in a radial direction.

In embodiments, the seal assembly includes a ring portion and first, second, third and fourth seal segments. The first, second, third, and fourth seal segments may be secured to the ring portion by connector portions. The connector portions may be living hinges. The smooth surfaces of the first, second, third, and fourth seal segments may face distally. The ribbed surfaces of the first, second, third, and fourth seal segments may face proximally. The smooth surfaces and the ribbed surfaces may alternate. The first seal segment may include a tab to facilitate assembly of the seal assembly. The plurality of seal segments may form a non-continuous inner seal circumference. The valve assembly may further include a centering mechanism for biasing the valve assembly toward a center of the cavity of the instrument valve housing.

A valve assembly includes a guard assembly and a seal assembly disposed distal of the guard assembly. The seal assembly includes a plurality of seal segments in an overlapping configuration. Each seal segment of the plurality of seal segments may include a seal portion having a smooth surface and a ribbed surface. The ribbed surfaces may include a plurality of ribs extending in a radial direction.

In embodiments, the seal assembly includes a ring portion and first, second, third and fourth seal segments. The first, second, third, and fourth seal segments are secured to the ring portion by connector portions. The connector portions may be living hinges. The smooth surfaces of the first, second, third, and fourth seal segments may face in a distal direction. The ribbed surfaces of the first, second, third, and fourth seal segments may face in a proximal direction. The smooth surfaces and the ribbed surface may alternate. The first seal segment may include a tab to facilitate assembly of the seal assembly. The plurality of seal segments may form a non-continuous inner seal circumference.

A seal assembly includes a ring portion, and a plurality of seal segments extending from the ring portion in an overlapping configuration. Each seal segment of the plurality of seal segments includes a seal portion having a smooth surface and a ribbed surface. The ribbed surfaces may include a plurality of ribs extending in a radial direction.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein:

FIG. 7 is an enlarged view of the indicated area of detail shown in FIG. 6;

FIG. 8 is a side cross-sectional view of the seal assembly shown in FIG. 4 taken along section line 8-8 in FIG. 4;

DETAILED DESCRIPTION

Figure 1:
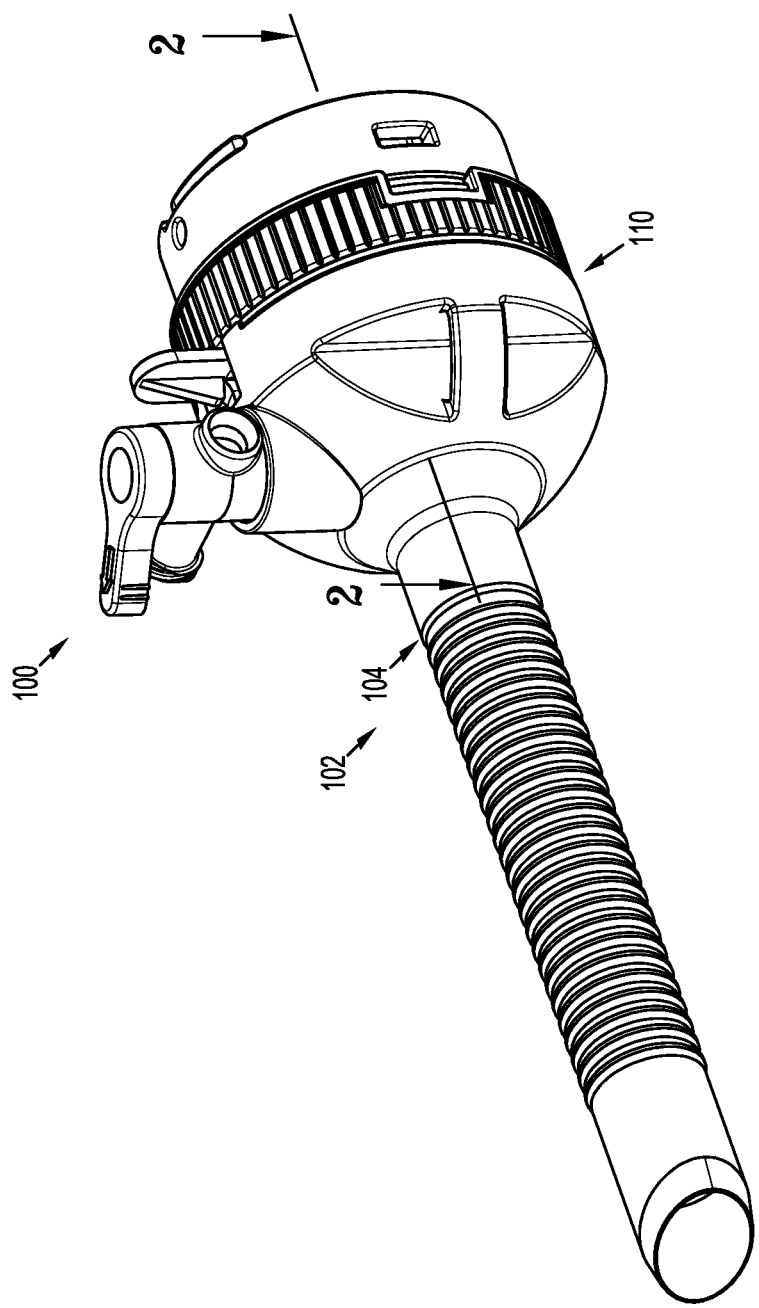
FIG. 1 is a side perspective view of a surgical access assembly according to an embodiment of the present disclosure.

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals refer to similar or identical elements throughout the description of the figures.

As used herein, the term "distal" refers to that portion of the instrument, or component thereof which is farther from the user while the term "proximal" refers to that portion of the instrument or component thereof which is closer to the user. As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

Surgical access assemblies with obturators are employed during minimally invasive surgery, e.g., laparoscopic surgery, and provide for the sealed access of surgical instruments into an insufflated body cavity, such as the abdominal cavity. The surgical access assemblies of the present disclosure include an instrument valve housing mounted on a cannula tube, and include an obturator (not shown) inserted through the valve housing and cannula. The obturator can have a blunt distal end, or a bladed or non-bladed penetrating distal end and can be used to incise the abdominal wall so that the surgical access assembly can be introduced into the abdomen. The handle of the obturator can engage or selectively lock into the instrument valve housing of the surgical access assembly.

Surgical access assemblies are employed to tunnel through an anatomical structure, e.g., the abdominal wall, either by making a new passage through the anatomical structure or by passing through an existing opening through the anatomical structure. Once the surgical access assembly with the obturator has tunneled through the anatomical structure, the obturator is removed, leaving the surgical access assembly in place. The instrument valve housing of the surgical access assembly includes valves that prevent the escape of insufflation fluid from the body cavity, while also allowing surgical instruments to be inserted into the body cavity.

In various embodiments, a bladeless optical trocar obturator may be provided that permits separation of tissue planes in a surgical procedure and visualization of body tissue fibers as they are being separated, thereby permitting a controlled traversal across a body wall. In other embodiments, the trocar obturator may be bladeless without being optical, e.g., without providing contemporaneous visualization thereof through the distal tip of an obturator. The bladeless obturator may be provided for the blunt dissection of the abdominal lining during a surgical procedure.

Various trocar obturators suitable for use with the surgical access assembly of the present disclosure are known and include, for example, bladed, bladeless, blunt, optical, and non-optical. For a detailed description of the structure and function of exemplary trocar assemblies, including exemplar trocar obturators and exemplar cannulas, please refer to PCT Publication No. WO 2016/186905 ("the '905 publication"), the content of which is hereby incorporated by reference herein in its entirety.

With initial reference now to FIG. 1, a surgical access assembly according to aspects of the present disclosure is shown generally as surgical access assembly 100. The surgical access assembly 100 includes a cannula 102 and an instrument valve housing 110 secured to the cannula 102. For a detailed description of an exemplary surgical access assembly, please refer to the '905 publication.

Figure 2:
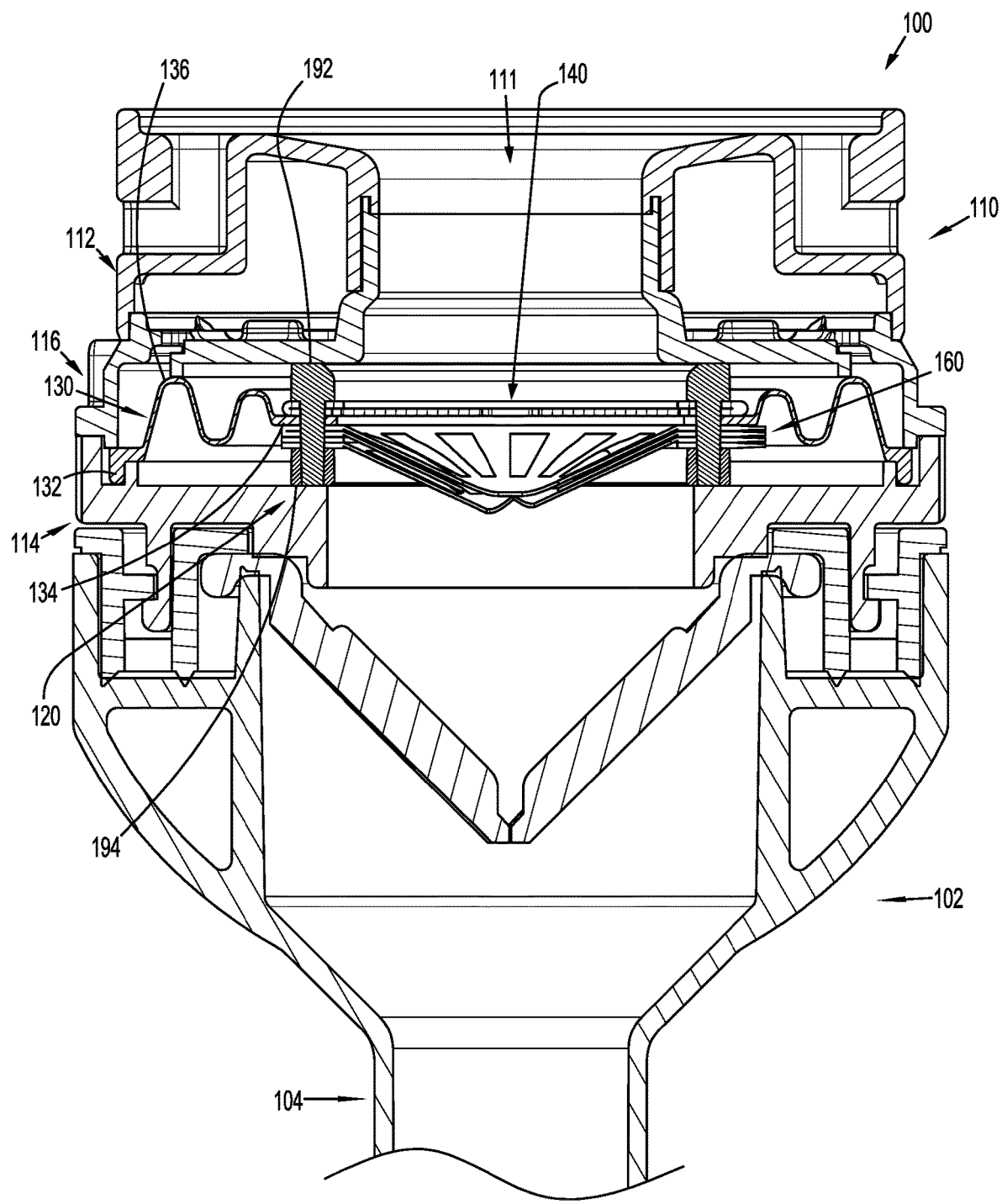
FIG. 2 a side cross-sectional view of the surgical access assembly shown in FIG. 1 taken along section line 2-2.

With reference to FIG. 2, the instrument valve housing 110 of the surgical access assembly 100 includes an upper housing section 112, a lower housing section 114, and an inner housing section 116. The upper, lower, and inner housing sections 112, 114, 116 are configured to support a valve assembly 120 on a proximal end of the cannula 102. More particularly, the inner housing section 116 is secured between the upper and lower housing sections 112, 114, and the valve assembly 120 is received between the inner and lower housing sections 116, 114. The upper and lower housing sections 112, 114 of the instrument valve housing 110 may be selectively attachable to, and detachable from, the inner housing section 116. The lower housing section 114 may be releasably or permanently attached to a cannula tube 104 (FIG. 1) of the cannula 102. In embodiments, either or both of the upper and lower housing sections 112, 114 of the instrument valve housing 110 may include knurls, indentations, tabs, or be otherwise configured to facilitate engagement by a clinician.

The surgical access assembly 100 may also include features for the stabilization of the surgical access assembly. For example, the distal end of the cannula tube 104 may carry a balloon anchor or another expandable member that engages the abdomen from the interior side. For example, see U.S. Pat. No. 7,300,448, the entire disclosure of which is hereby incorporated by reference herein. A feature on the opposite side of the abdominal wall may be used to further stabilize the surgical access assembly, such as adhesive tabs or adjustable foam collars.

The upper, lower, and inner housing sections 112, 114, 116 of the instrument valve housing 110 define a longitudinal passage 111 for receipt of a surgical instrument (not shown). The valve assembly 120 is supported within the instrument valve housing 110 to provide sealed passage of the surgical instrument (not shown) through the surgical access assembly 100.

Figure 3:
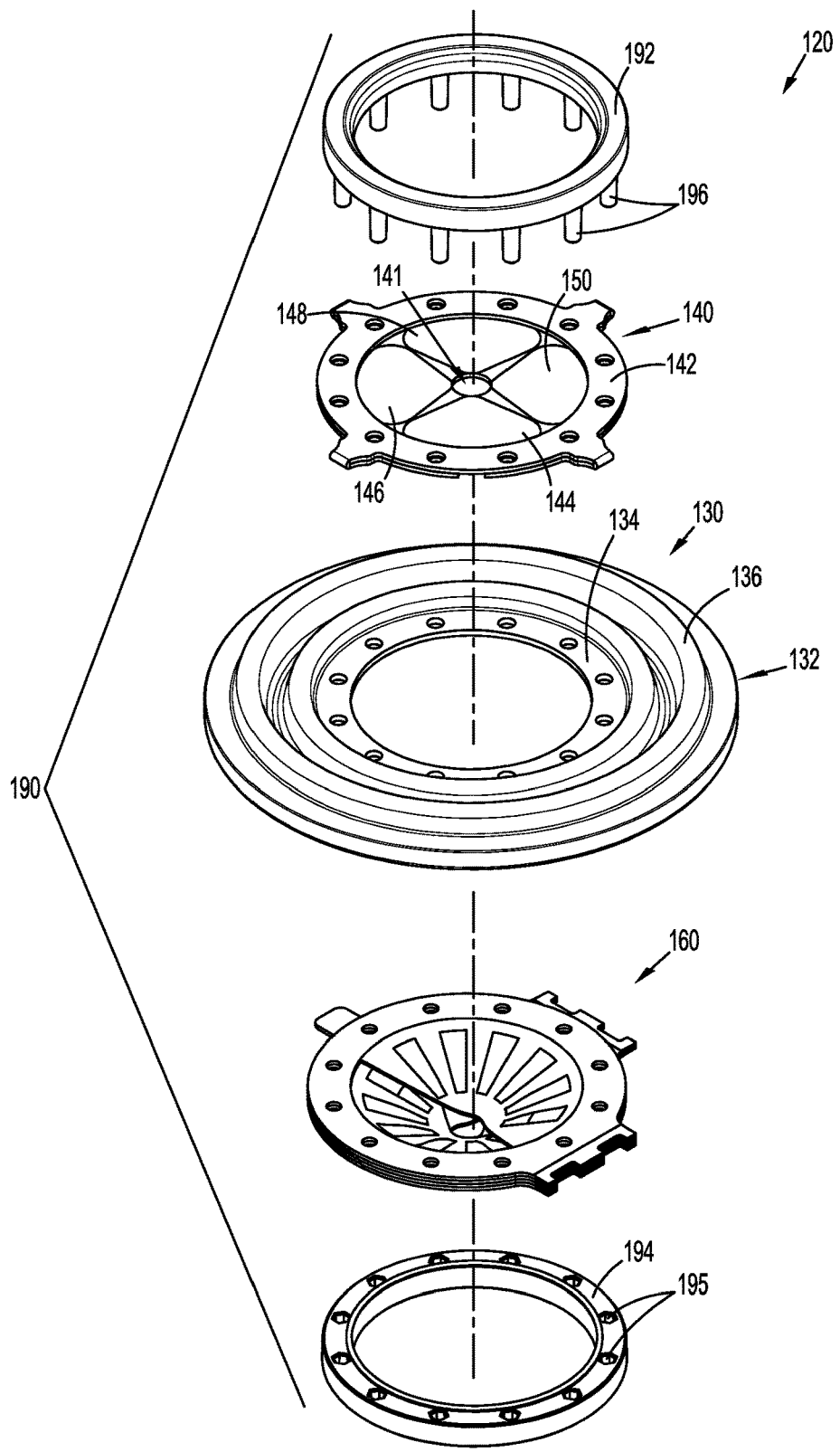
FIG. 3 is an exploded perspective view of a valve assembly, with parts separated, including a centering mechanism, a guard assembly, a seal assembly, and a retainer assembly.

With particular reference to FIGS. 2 and 3, the valve assembly 120 supported in the instrument valve housing 110 (FIG. 2) includes a centering mechanism 130, a guard assembly 140, a seal assembly 160, and a retainer assembly 190. The centering mechanism 130 of the valve assembly 120 permits radial movement of the valve assembly 120 relative to the instrument valve housing 110 when a surgical instrument is received through the valve assembly 120, and returns the valve assembly 120 to a generally centered position once the surgical instrument is withdrawn from within the instrument valve housing 110. The guard assembly 140 protects the seal assembly 160 during insertion and withdrawal of a surgical instrument through the seal assembly 160. The seal assembly 160 provides sealed passage of the surgical instrument through the instrument valve housing 110. The retainer assembly 190 maintains the centering mechanism 130, the guard assembly 140, and the seal assembly 160 in an aligned relationship with one another.

With continued reference to FIGS. 2 and 3, as noted above, the centering mechanism 130 of the valve assembly 120 is configured to maintain the valve assembly 120 centered within the instrument valve housing 110 (FIG. 2) in the absence of a surgical instrument passing through the valve assembly 120. In embodiments, and as shown, the centering mechanism 130 includes an outer annular ring 132, an inner annular ring 134, and a bellows 136 disposed between the outer annular ring 132 and the inner annular ring 134. As shown in FIG. 2, the outer annular ring 132 is received between the inner housing section 116 and the lower housing section 114 to retain the centering mechanism 130 within the instrument valve housing 110. The inner annular ring 134 supports the guard assembly 140. For a detailed description of the structure and function of an exemplary centering mechanism, please refer to U.S. Pat. No. 6,702,787, the content of which is incorporated herein by reference in its entirety.

Although shown including the centering mechanism 130 having bellows 136, the valve assembly 120 may include alternative centering mechanisms. For example, the centering mechanism may include an annular base and a plurality of spokes extending from the base, as described in U.S. Pat. App. Pub. No. 2015/0025477 ("the '477 publication"), the content of which is incorporated herein by reference in its entirety. It is envisioned that the centering mechanism may include multiple sets of spokes, as disclosed in the '477 publication.

With continued reference to FIGS. 2 and 3, the guard assembly 140 of the valve assembly 120 is configured to protect the seal assembly 160 as a surgical instrument (not shown) passes through the instrument valve housing 110 (FIG. 2).

The guard assembly 140 includes a ring portion 142 and first, second, third, and fourth petals 144, 146, 148, 150. The first, second, third, and fourth petals 144, 146, 148, 150 define an opening 141 therebetween to facilitate sealed passage of a surgical instrument (not shown) through the guard assembly 140. Although shown including six (4) petals, it is envisioned that the guard assembly may include any suitable number of petals, and the petals may include flap portions of any size or configuration. For exemplary guard assemblies, as well as other aspects of surgical access assemblies, please refer to U.S. Pat. Nos. 5,895,377 and 6,569,120 ("the '377 and '120 patents"), the entire disclosures of which are hereby incorporated by reference herein. For detailed description of the structure and function of other exemplary guard assemblies, please refer to commonly owned U.S. Pat. App. Pub. Nos. 2020/0214740A1, 2020/0337723A1, and 2021/0113240A1, the entire disclosures of which are incorporated herein by reference in its entirety.

Figure 4:
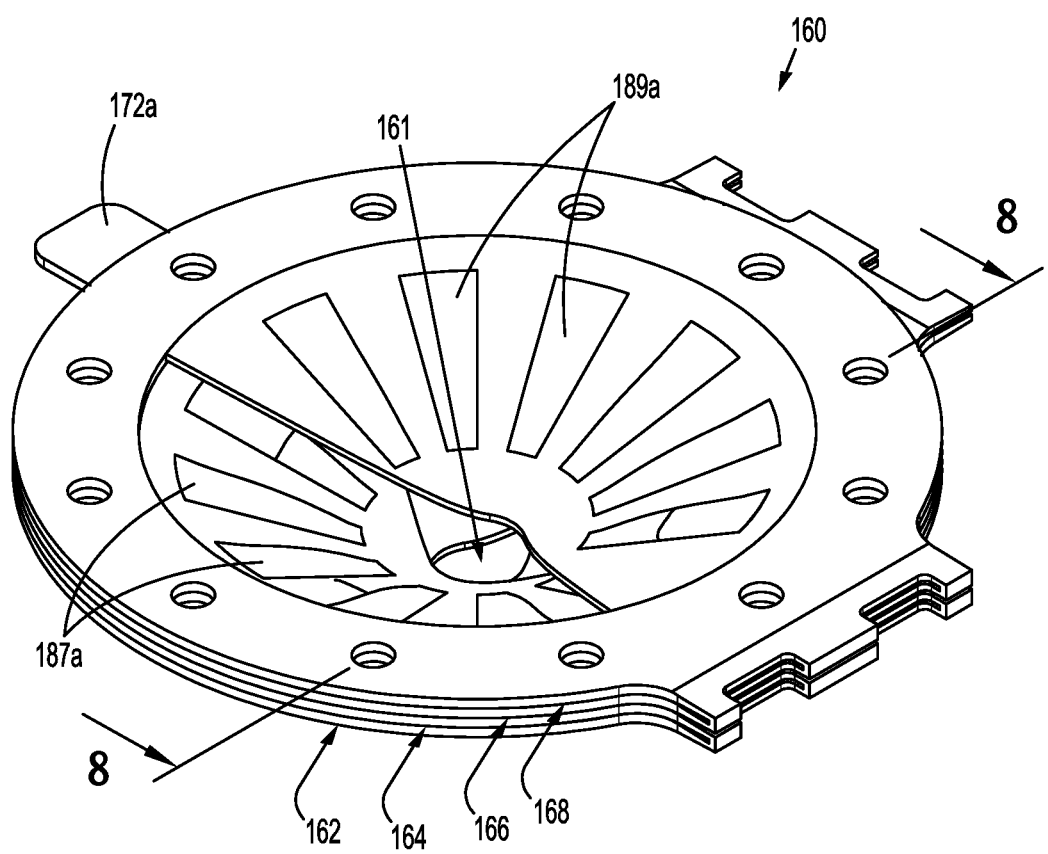
FIG. 4 is a top perspective view of the seal assembly shown in FIG. 3.
Figure 5:
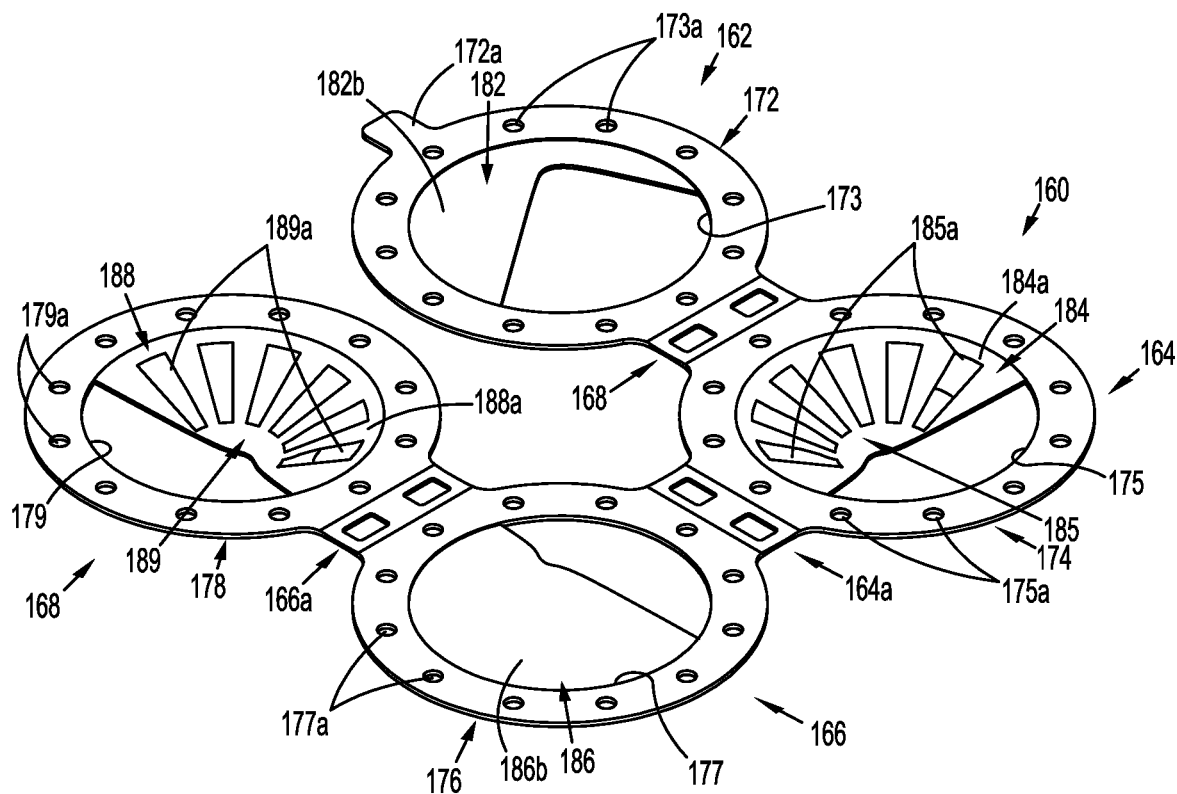
FIG. 5 is a perspective view of the seal assembly shown in FIG. 4, in an initial or unfolded condition.
Figure 6:
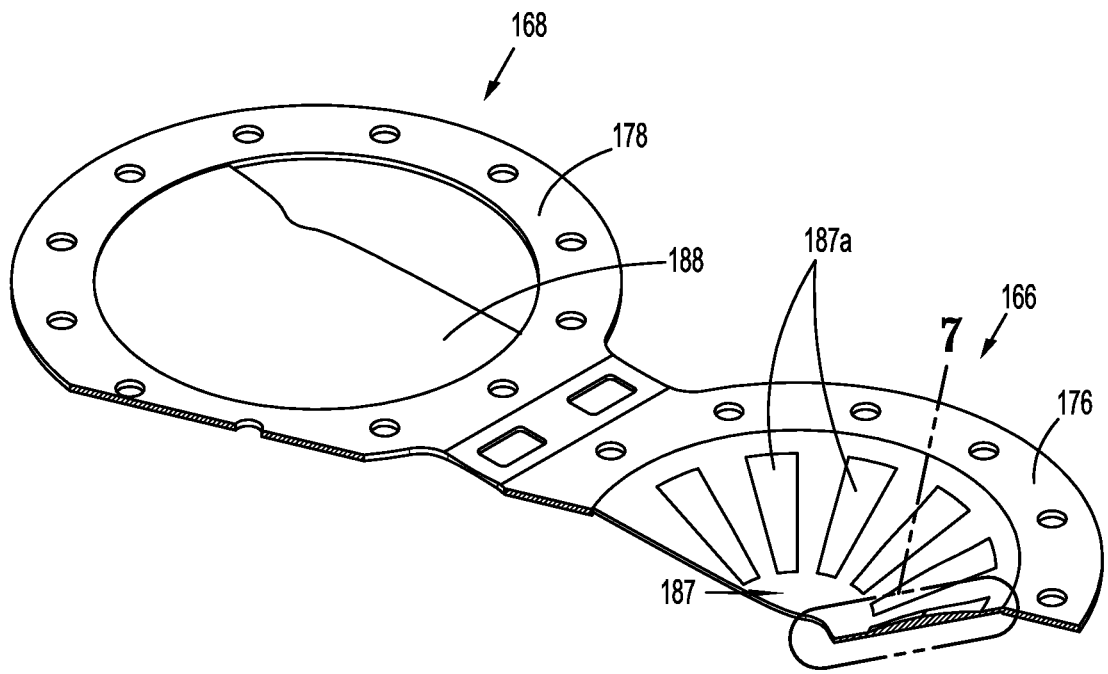
FIG. 6 is a side cross-sectional view of the seal assembly shown in FIG. 4 taken along section line 6-6 in FIG. 9.

Referring to FIGS. 4-6, the seal assembly 160 of the valve assembly 120 is configured to provide a seal around an outer surface of a surgical instrument passing through the instrument valve housing 110 (FIG. 1). In embodiments, and as shown, the seal assembly 160 forms a conical seal body; however, it is envisioned that the aspects of the present disclosure may be modified for use with a flat seal body.

The seal assembly 160 includes first, second, third, and fourth seal segments 162, 164, 166, 168 each having a base or ring portion 172, 174, 176, 178, respectively, and a respective seal portion 182, 184, 186, 188 supported by the respective ring portion 172, 174, 176, 178. The first and second seal segments 162, 164, the second and third seal segments 164, 166, and the third and fourth seal segments 166, 168, are connected to one another by a connector portion 162a, 164a, 166a, respectively. The connector portions 162a, 164a, 166a may include a living hinge, or be otherwise configured to permit folding of the respective first, second, third, and fourth seal segments 162, 164, 166, 168 with respect to each other.

The seal portions 182, 184, 186, 188 of the respective first, second, third, and fourth seal segments 162, 164, 166, 168 of the seal assembly 160 are formed of an elastic material, e.g., rubber, and define a semi-conical configuration when the seal assembly 160 is in the folded condition. As noted above, the seal portions 182, 184, 186, 188 may alternatively define a flat seal. In embodiments, the seal portions 182, 184, 186, 188 are formed of polyurethane, polyisoprenes, or silicone elastomers. The ring portions 172, 174, 176, 178 of the respective first, second, third, and fourth seal segments 162, 164, 166, 168 of the seal assembly 160 may be formed of the same or different materials as the respective seal portions 182, 184, 186, 188. In embodiments, the seal portions 182, 184, 186, 188 may include one or more fabric layers.

The ring portions 172, 174, 176, 178 of the respective first, second, third, and fourth seal segments 162, 164, 166, 168 of the seal assembly 160 define openings 173, 175, 177, 179, respectively, and a plurality of openings 173a, 175a, 177a, 179a corresponding to a plurality of pins 196 (FIG. 13) extending from an upper retainer member 192 of the retainer assembly 190. In embodiments, and as shown, the ring portion 172 of the first seal section 162 may include a tab 172a to facilitate assembly and/or positioning of the seal assembly 160.

The seal portions 182, 184, 186, 188 of the respective first, second, third, and fourth seal segments 162, 164, 166, 168 of the seal assembly 160 define a central opening 161 and are configured to receive a surgical instrument (not shown) through the valve assembly 120 in a sealed manner. The seal portions 182, 184, 186, 188, form a non-continuous or virtual seal circumference to reduce tearing during insertion, manipulation, and/or withdrawal of a surgical instrument (not shown) through the valve assembly 120.

An inner edge of the seal portions 182, 184, 186, 188 of the respective first, second, third, and fourth seal segments 162, 164, 166, 168 of the seal assembly 160 forms an angle "α" (FIG. 9) between about one-hundred eighty degrees (180°) and about two-hundred twenty degrees (220°). In this manner, each seal portion 182, 184, 186, 188 occupies at least fifty percent (50%) of the respective opening 173, 175, 177, 179 in the ring portions 172, 174, 176, 178, respectively.

Figure 9:
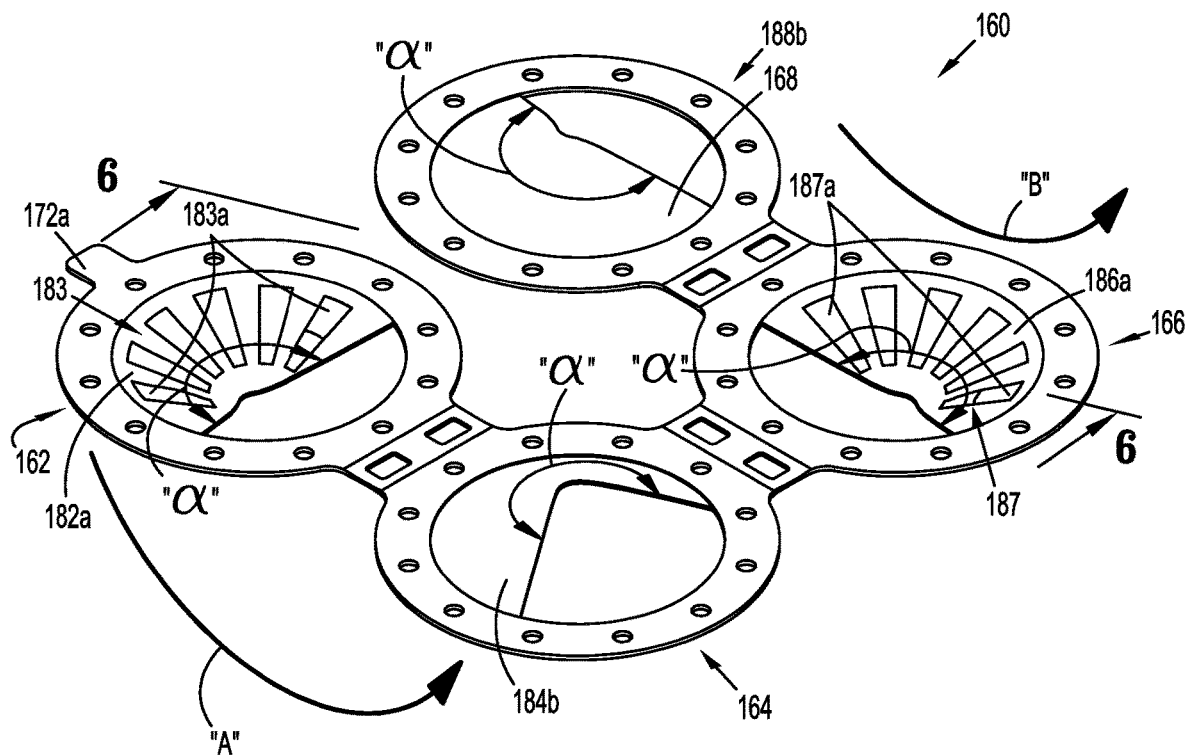
FIG. 9 is a bottom perspective view of the seal assembly shown in FIG. 4, in the initial or unfolded condition.

With particular reference to FIGS. 5 and 9, the seal portions 182, 184, 186, 188 of the respective first, second, third, and fourth sections 162, 164, 166, 168 of the seal assembly 160 includes a first or ribbed surface 182a, 184a, 186a, 188a and a second or smooth surface 182b, 184b, 186b, 188b. When the seal assembly 160 is in a folded condition (FIG. 4), the ribbed surfaces 182a, 184a, 186a, 188a face proximally and the smooth surfaces 182b, 184b, 186b, 188b face distally. In this manner, the smooth surfaces 182b, 184b, 186b of the respective seal portions 182, 184, 186 of the first, second and third seal segments 162, 164, 166, respectively, engage the ribbed surfaces 184a, 186a, 188a of the respective seal portions 184, 186, 188 of the second, third, and fourth seal segments 164, 166, 168.

The ribbed surfaces 182a, 184a, 186a, 188a of the respective seal portions 182, 184, 186, 188 of the first, second, third, and fourth seal segments 162, 164, 166, 168, respectively, include a plurality of raised portions or ribs 183, 185, 187, 189. Each rib 183a, 185a, 187a, 189a of the plurality of ribs 183, 185, 187, 189 extends in a radial direction. In embodiments, and as shown in FIG. 7, each rib 183a, 185a, 187a, 189a is tapered on leading and trailing portions. Alternatively, each rib 183a, 185a, 187a, 189a may have only a leading or trailing tapered portion, or instead may include a consistent thickness.

The plurality of ribs 183, 185, 187, 189 of the ribbed surface 182a, 184a, 186a, 188a of the respective seal portions 182, 184, 186, 188 of the first, second, third, and fourth seal segments 162, 164, 166, 168, respectively, create extra padding along the ribbed surfaces 182a, 184a, 186a, 188a to reduce the likelihood of tearing the seal assembly during insertion, manipulation, and/or withdrawn of a surgical instrument (not shown) through the seal assembly 160. The plurality of ribs 183, 185, 187, 189 are arranged such then when the seal assembly 160 is in the folded condition (FIG. 4) the seal portions 182, 184, 186, 188 form a seal having a increased uniform thickness. The increased uniform thickness of the seal and/or the reinforcement provided by the plurality of ribs 183, 185, 187, 189 to the respective seal portions 182, 184, 186, 188 reduces the possibility of a surgical instrument (not shown) puncturing the seal portions 182, 184, 186, 188, thereby reducing the likelihood of tearing. This design also limits additional potential leak paths.

The method of folding the seal assembly 160 will now be described with reference to FIGS. 9-11. Referring initially to FIG. 9, the first seal section 162 of the seal assembly 160 is folded relative to the second seal section 164 of the seal assembly 160, as indicated by arrow "A", such that the smooth surface 182b (FIG. 5) of the first seal section 162 overlaps the ribbed surface 184a (FIG. 5) of the second seal section 164. Similarly, the fourth seal section 168 of the seal assembly 160 is folded relative to the third seal section 166 of the seal assembly 160, as indicated by arrow "B", such that the ribbed surface 188a (FIG. 5) of the fourth section 168 overlaps the smooth surface 186b (FIG. 5) of the third seal section 166.

Figure 10:
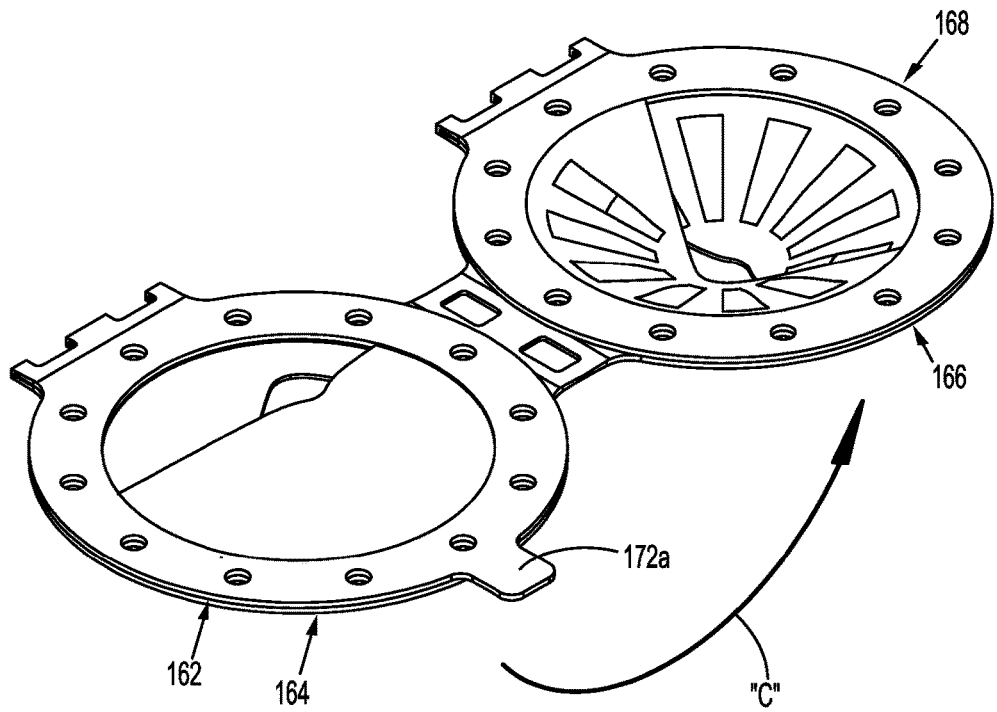
FIG. 10 is a top perspective view of the seal assembly shown in FIG. 4, in a partially folded condition.
Figure 11:
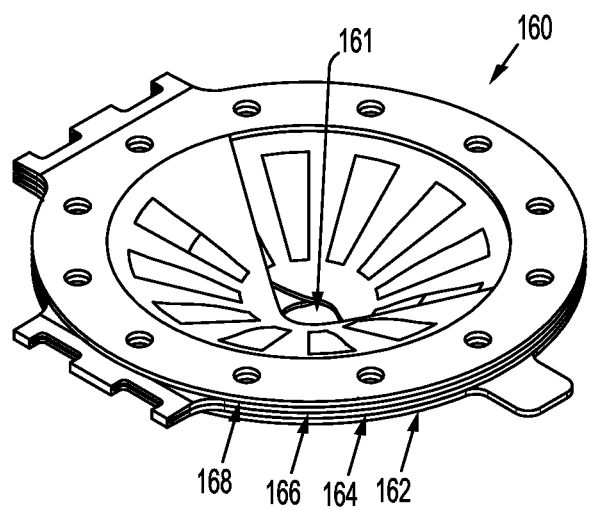
FIG. 11 is a top perspective view of the seal assembly shown in FIG. 4, in fully folded condition.

Turning to FIG. 10, the first and second seal segments 162, 164 of the seal assembly 160 are then folded relative to the third and fourth seal segments 166, 168 of the seal assembly 160, as indicated by arrow "C", such that the ribbed surface 184a (FIG. 5) of the second seal section 164 overlaps the smooth surface 186b (FIG. 5) of the third section 166.

Figure 12:
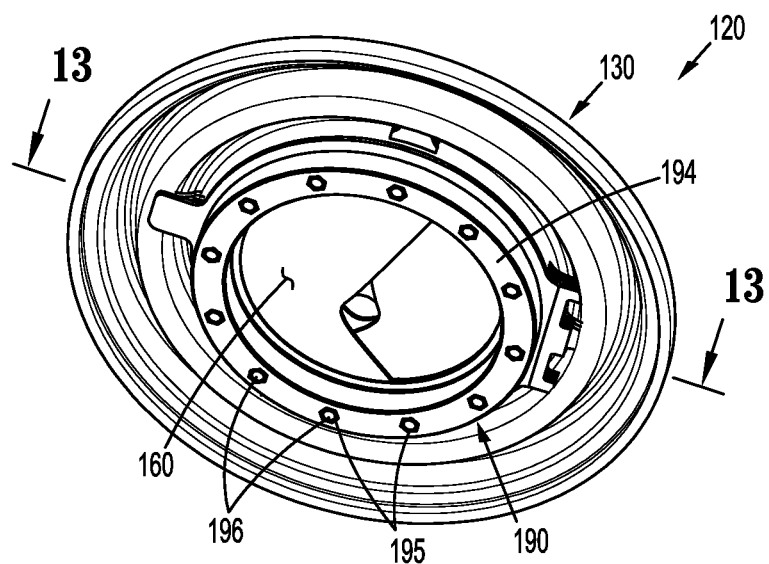
FIG. 12 is a bottom perspective view of the seal assembly shown in FIG. 3.
Figure 13:
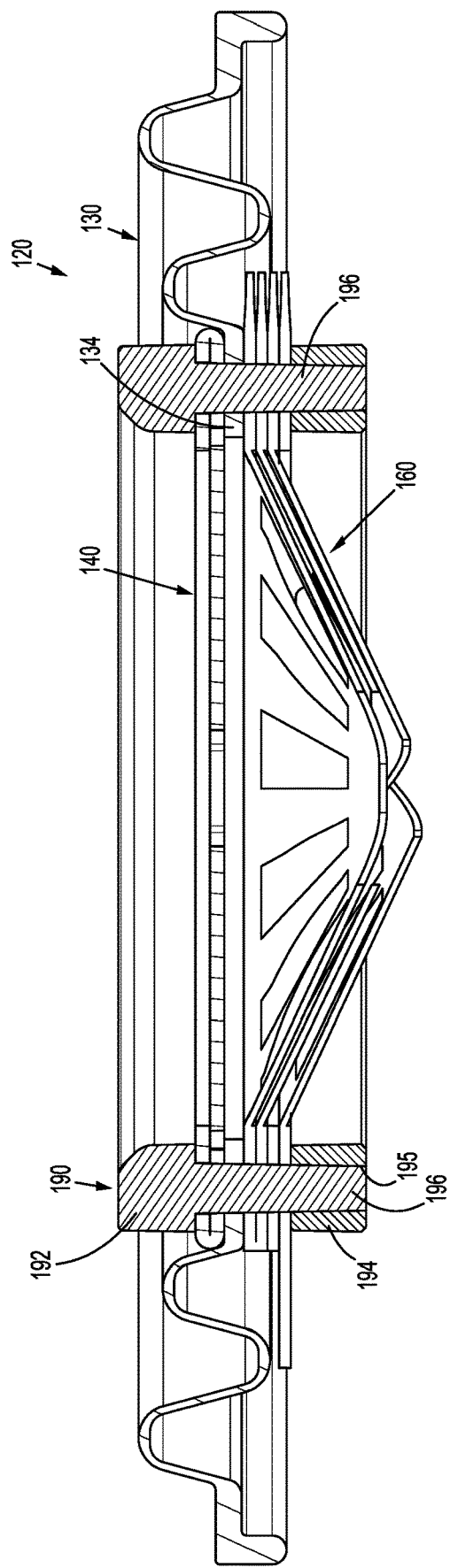
FIG. 13 is a side cross-sectional view of the valve assembly shown in FIG. 3 taken along section line 13-13 in FIG. 12.

With reference to FIGS. 12 and 13, the retainer assembly 190 (of the valve assembly 120) is configured to secure the guard assembly 140 relative to the seal assembly 160, and secure the guard and seal assemblies 140, 160 to the centering mechanism 130. The retainer assembly 190 includes an upper retainer member 192, and a lower retainer member 194.

As noted above, the upper retainer member 192 of the retainer assembly 190 includes a plurality of pins 196. The plurality of pins 196 extends from a bottom surface of the upper retainer member 192 (FIG. 13). Each pin 196 of the plurality of pins 196 is configured to be lockingly received within an opening 195 of a plurality of openings 195 of the lower retainer member 194. In embodiments, the plurality of pins 196 is welded, glued, adhered, bonded or otherwise secured within the plurality of openings 195 in the lower retainer member 194 to secure the upper retainer member 192 and the lower retainer member 194 together. Alternatively, the lower retainer member 194 may instead, or additionally, include a plurality of pins (not shown) with the upper retainer member 192 defining a plurality corresponding openings (not shown). Either or both of the upper and lower retainer members 192, 194 may include locking features (not shown) for engaging the plurality of pins and securing the upper retainer member 192 to the lower retainer member 194.

With continued reference to FIGS. 12 and 13, the plurality of pins 196 of the upper retainer member 192 extends through the ring portion 142 of the guard assembly 140, through the inner annular ring 134 of the centering mechanism 130, through the seal assembly 160, and into the plurality of openings 195 in the lower retainer member 194. As noted above, placing the guard assembly 140 proximal of the seal assembly 160 reduces or eliminates potential damage to the seal assembly 160 during insertion and retraction of a surgical instrument through the seal assembly 160. The placement of the guard assembly 140 also reduces the potential of the seal assembly 160 disintegrating into the body cavity during minimally invasive procedures.

During a surgical procedure utilizing surgical access assembly 100 (FIG. 1), a surgical instrument (not shown) is introduced into the instrument valve housing 110 through the longitudinal passage 111 in the upper, lower, and inner housing sections 112, 114, 116 (FIG. 2). As described in the'377 and '120 patents, the distal end of the surgical instrument engages the first, second, third, and fourth petals 144, 146, 148, 150 (FIG. 3) of the guard assembly 140 causing flaps of the respective first, second, third, and fourth petals 144, 146, 148, 150 to flex downward into contact with the seal assembly 160 to cause the central opening 161 of the seal assembly 160 to open to accommodate passage of the surgical instrument through the seal assembly 160. The guard assembly 140 minimizes damage to the seal assembly 160 during insertion of an instrument through the valve assembly 120

As noted above, the plurality of ribs 183, 185, 187, 189 of the ribbed surface 182a, 184a, 186a, 188a of the respective seal portions 182, 184, 186, 188 of the first, second, third, and fourth seal segments 162, 164, 166, 168, respectively, create extra padding along the ribbed surface 182a, 184a, 186a, 188a to reduce the likelihood of tearing the seal assembly during insertion, manipulation, and/or withdrawn of a surgical instrument (not shown) through the seal assembly 160.

While various embodiments of the present disclosure have been shown and described herein, it will be obvious to those skilled in the art that these embodiments are provided by way of example only. Numerous variations, changes, and substitutions will now occur to those skilled in the art without departing from the present disclosure. Accordingly, it is intended that the invention be limited only by the spirit and scope of the appended claims.

What is claimed is:

1. An access assembly comprising:
   an instrument valve housing including upper, lower, and inner housing sections and defining a cavity; and
   a valve assembly disposed within the cavity of the instrument valve housing, the valve assembly including:
   a guard assembly;
   a seal assembly disposed distal of the guard assembly, the seal assembly including a ring portion and a plurality of seal segments extending from the ring portion in an overlapping configuration, each seal segment of the plurality of seal segments including a seal portion having a smooth surface and a ribbed surface, wherein the smooth surfaces and the ribbed surfaces alternate and the ribbed surfaces include a plurality of ribs extending in a radial direction; and
   a retainer assembly securing the guard assembly relative to the seal assembly, wherein the plurality of seal segments includes four seal segments.

2. The access assembly of claim 1, wherein the four seal segments are secured to the ring portion by connector portions.

3. The access assembly of claim 2, wherein the connector portions are living hinges.

4. The access assembly of claim 2, wherein the smooth surface of each of the four seal segments faces distally.

5. The access assembly of claim 1, wherein the ribbed surface of each of the four seal segments faces proximally.

6. The access assembly of claim 1, wherein one of the four seal segments includes a tab to facilitate assembly of the seal assembly.

7. The access assembly of claim 1, wherein the plurality of seal segments form a non-continuous inner seal circumference.

8. The access assembly of claim 1, further including a centering mechanism for biasing the valve assembly toward a center of the cavity of the instrument valve housing.

9. An access assembly for receiving an instrument through the access assembly in a sealed manner, the access assembly comprising:
a valve assembly including,
a guard assembly having a plurality of overlapping petals; and
a seal assembly disposed distal of the guard assembly, the seal assembly including a plurality of ring portions and a plurality of seal segments in an overlapping configuration, each seal segment of the seal segment extending from each ring portion of the plurality of ring portions and folded including a seal portion having a smooth surface and a ribbed surface, wherein the ribbed surfaces include a plurality of ribs extending in a radial direction, wherein the plurality of ring portions includes more than two ring portions.

10. The valve assembly of claim 9, wherein the seal assembly includes ring portions and first, second, third and fourth seal segments.

11. The valve assembly of claim 10, wherein the first, second, third, and fourth seal segments are each secured to the respective ring portion by a connector portion.

12. The valve assembly of claim 11, wherein the connector portions are living hinges.

13. The valve assembly of claim 10, wherein the smooth surfaces of the first, second, third, and fourth seal segments face in a distal direction.

14. The valve assembly of claim 10, wherein the ribbed surfaces of the first, second, third, and fourth seal segments face in a proximal direction.

15. The valve assembly of claim 10, wherein the first seal segment includes a tab to facilitate assembly of the seal assembly.

16. The valve assembly of claim 9 wherein the smooth surfaces and the ribbed surface alternate.

17. The valve assembly of claim 9, wherein the plurality of seal segments form a non-continuous inner seal circumference.

18. A seal assembly for an access assembly for receiving an instrument through the access assembly in a sealed manner, the seal assembly comprising:
a ring portion; and
a plurality of seal segments extending from the ring portion in an overlapping configuration, each seal segment of the plurality of seal segments including a seal portion having a smooth surface a ribbed surface, an outer portion in engagement with the ring portion, and an inner portion defining a section of an opening, the inner portions of the plurality of seal segments forming a non-continuous inner seal circumference to reduce tearing by instruments received through the seal assembly, wherein the ribbed surfaces include a plurality of elongate ribs extending from the inner portion to the outer portion, wherein the plurality of seal segments includes four seal segments.

* * * * *